US010076350B2

(12) United States Patent
Cao et al.

(10) Patent No.: US 10,076,350 B2
(45) Date of Patent: Sep. 18, 2018

(54) TOOL BIT OF ULTRASONIC OSTEOTOME AND ULTRASONIC OSTEOTOME INCLUDING THE SAME

(71) Applicants: Qun Cao, Beijing (CN); Chunyuan Li, Beijing (CN)

(72) Inventors: Qun Cao, Beijing (CN); Chunyuan Li, Beijing (CN)

( * ) Notice: Subject to any disclaimer, the term of this patent is extended or adjusted under 35 U.S.C. 154(b) by 193 days.

(21) Appl. No.: 14/997,750

(22) Filed: Jan. 18, 2016

(65) Prior Publication Data

US 2016/0128716 A1 May 12, 2016

Related U.S. Application Data

(63) Continuation of application No. PCT/CN2014/079580, filed on Jun. 10, 2014.

(30) Foreign Application Priority Data

Jul. 22, 2013 (CN) ..................... 2013 2 0435092 U

(51) Int. Cl.
*A61B 17/32* (2006.01)
*A61B 17/16* (2006.01)
(Continued)

(52) U.S. Cl.
CPC .... *A61B 17/320068* (2013.01); *A61B 17/142* (2016.11); *A61B 17/144* (2016.11);
(Continued)

(58) Field of Classification Search
CPC . A61B 17/142; A61B 17/144; A61B 17/1604; A61B 17/1659; A61B 17/32;
(Continued)

(56) References Cited

U.S. PATENT DOCUMENTS 4,838,899 A * 6/1989 Bifuk ..................... A61B 17/32
451/540
5,318,570 A 6/1994 Hood et al.
(Continued)

FOREIGN PATENT DOCUMENTS

CN 201070394 Y 6/2008
CN 102176874 A 9/2011
(Continued)

OTHER PUBLICATIONS

Australian Patent Examination Report No. 1 for Australian patent application No. 2014295671; Australian Government; IP Australia; dated Sep. 10, 2016.
(Continued)

*Primary Examiner* — Larry E Waggle, Jr.
(74) *Attorney, Agent, or Firm* — Thomas E. Lees, LLC

(57) ABSTRACT

Disclosed are a tool bit of an ultrasonic osteotome and an ultrasonic osteotome including the same, the tool bit comprising: an arbour (2); and an end portion (1) of the tool bit connected to a front end of arbour (2), wherein the end portion (1) of the tool bit has a hook-like shape and includes a hook tip (11), a hook handle (13), as well as a hook-shaped interconnecting piece (12) which is interconnected between the hook tip (11) and the hook handle (13). The hook handle (13) is connected with the arbour (2), and the inner side edge of the hook-shaped interconnecting piece (12) is tooth-like. With this ultrasonic osteotome, the cutting efficiency is high and surgery time is short, therefore the labour intensity of medical workers is decreased. Moreover, accurate positioning can be realized in cutting process with no skidding, so the chance of success of surgery can be improved.

9 Claims, 6 Drawing Sheets

(51) Int. Cl.
  *A61B 17/3205* (2006.01)
  *A61B 17/3209* (2006.01)
  *A61B 17/14* (2006.01)
(52) U.S. Cl.
  CPC ...... *A61B 17/1604* (2013.01); *A61B 17/1659* (2013.01); *A61B 17/32* (2013.01); *A61B 17/3205* (2013.01); *A61B 17/3209* (2013.01); *A61B 2017/320072* (2013.01); *A61B 2017/320075* (2017.08)
(58) Field of Classification Search
  CPC ........... A61B 17/320068; A61B 2017/320072; A61B 2017/320075; A61B 17/3205; A61B 17/3209
  See application file for complete search history.

(56) References Cited

U.S. PATENT DOCUMENTS

| | | | | |
|---|---|---|---|---|
| D620,595 | S | * | 7/2010 | Pinel ........................... D24/144 |
| 2004/0023187 | A1 | * | 2/2004 | Hickok .................... A61C 3/03 433/119 |
| 2011/0125174 | A1 | | 5/2011 | Babaev |
| 2013/0090660 | A1 | * | 4/2013 | Darian ............ A61B 17/32 606/84 |

FOREIGN PATENT DOCUMENTS

| | | | | |
|---|---|---|---|---|
| CN | 202458600 | U | | 10/2012 |
| CN | 202740088 | U * | 2/2013 | ......... A61B 17/3211 |
| CN | 202920294 | U | | 5/2013 |
| CN | 203354613 | U | | 12/2013 |
| EP | 1736107 | A1 | | 12/2006 |
| JP | 2006-263031 | A | | 10/2006 |
| JP | 2012-501735 | A | | 1/2012 |

OTHER PUBLICATIONS

Supplementary European Search Report for European patent application No. 14829688.2; European Patent Office; dated Dec. 9, 2016.
Korean Patent Examination Report for Korean patent application No. KR20-2016-7000006; Korean Patent Office; dated Jan. 10, 2017.
Written Opinion of the International Searching Authority for PCT Application No. PCT/CN2014/079580; dated Sep. 17, 2014.
International Search Report for PCT Application No. PCT/CN2014/079580; dated Sep. 16, 2014; State Intellectual Property Office of the P. R. China; Beijing, China; English translation included.

* cited by examiner

TOOL BIT OF ULTRASONIC OSTEOTOME AND ULTRASONIC OSTEOTOME INCLUDING THE SAME

CROSS REFERENCE TO RELATED APPLICATIONS

This is a Continuation application of International Application Serial No. PCT/CN2014/079580 filed on Jun. 10, 2014, which claims the benefit of Chinese Application No. 201320435092.7 filed on Jul. 22, 2013, the disclosures of which are hereby incorporated by reference.

BACKGROUND

1. Field of the Invention

The present disclosure relates to a technical field of medical equipment, in particular to an improved tool bit of ultrasonic osteotome and an ultrasonic osteotome comprising the tool bit.

2. Description of the Related Art

In osteopathic surgery, an ultrasonic osteotome is usually used to perform cutting, grinding, planning, scraping, even arbitrary shaping on bones. FIG. 1A shows a typical structure of a conventional tool bit 100' of ultrasonic osteotome, which has a plurality of teeth and a wide tip, and a majority part of the tip does not constitute an effective main cutting part, as shown in FIG. 1B.

The tool bit 100' also has the following defects. As illustrated in FIG. 2A, when the tool bit 100' is used, a force needs to be applied to osseous tissue of a bone 200', as indicated by F1 in FIG. 2A. When the cutting operation is desired, the tool bit 100' needs to apply the force downwardly to the osseous tissue, which may not only cause a low cutting speed and a low efficiency, but also cause the tool bit with a plurality of teeth to break in operation, as indicated by F2 in FIG. 2B. However, in the process of a surgery, the tool bit 100' of ultrasonic osteotome may be inserted into tissue 300' such as marrow etc. accidentally, which brings unretrievable injury for a patient. Moreover, the tool bit 100' of ultrasonic osteotome has a complex shape and is difficult to be machined, thus, the production cost thereof is high.

BRIEF SUMMARY

The present disclosure aims at solving the above problems in the prior art.

Further, the present disclosure provides a tool bit of an ultrasonic osteotome that not only has high operating efficiency but also has high cutting speed, so as to improve the chance of success in surgery.

Further, the present disclosure provides a tool bit of an ultrasonic osteotome that can be accurately positioned in operating process, so as to improve the chance of success in surgery.

Moreover, the present disclosure also provides an ultrasonic osteotome including the tool bit as described above.

In accordance with an embodiment, a tool bit of an ultrasonic osteotome, comprising: an arbor; and an end portion of the tool bit connected to a front end of said arbor, said end portion of the tool bit has a hook-like shape and includes a hook tip, a hook handle, as well as a hook-shaped interconnecting piece which is interconnected between said hook tip and said hook handle, wherein said hook handle is connected with said arbor, and the inner side edge of said hook-shaped interconnecting piece is tooth-like.

In the tool bit of an ultrasonic osteotome according to an embodiment of the present invention, the hook tip can be employed to cut bones, so that cutting efficiency is high and surgery time is short. Therefore, the labour intensity of medical workers is decreased. Moreover, accurate positioning can be realized in cutting process, with no skidding, so the chance of success of surgery can be improved. Furthermore, the ultrasonic osteotome according to the embodiment of the present invention is exquisitely and compactly designed, and the cutting amount and cutting shape for the bone can be controlled accurately, so the bone wastage resulting from cutting in surgery may be decreased. In addition, the ultrasonic osteotome according to the embodiment of the present invention has a hemostasis effect, so the amount of bleeding is decreased. Besides that, the tool bit of the ultrasonic osteotome according to the embodiment of the present invention can be machined easily with low manufacture cost.

In addition, the tool bit according to an embodiment of the present invention may also comprise the following additional technical features:

In accordance with some embodiments of the present invention, the outer side edge of said hook-shaped interconnecting piece is tooth-like.

In accordance with an embodiment of the present invention, the end portion of the tool bit is structured to have a tabular hook-like shape.

In accordance with an embodiment of the present invention, the cross section of said hook handle increases gradually in the direction from said hook-shaped interconnecting piece to said arbor.

In accordance with an embodiment of the present invention, the cross section of said hook tip is formed in a way that the wider end portion of said hook tip is connected with the other side of said hook valley.

In accordance with an embodiment of the present invention, said tool bit of the ultrasonic osteotome further includes a bit body connected to said arbor, said bit body and said arbor are connected via an arc transition, and said bit body is provided with a wrench-operation position.

In accordance with an embodiment of the present invention, said arbor and said end portion of the tool bit are formed as an integral part.

In accordance with an embodiment of the present invention, said end portion of the tool bit, said arbor and said bit body are formed as an integral part.

In accordance with an embodiment of the present invention, among the teeth provided on the inner side of said hook-shaped interconnecting piece, tooth pitch of adjacent said teeth increases gradually from said hook tip to said hook handle.

In accordance with the second aspect of present invention, there provides a tool bit of an ultrasonic osteotome, comprising: an arbor; and an end portion connected to one end of said arbor, said end portion being hook-like, wherein said end portion includes a hook tip, a hook valley, and a hook handle, the edge of said hook valley is tooth-like.

In accordance with the third aspect of present invention, there further provides an ultrasonic osteotome comprising the tool bit mentioned above.

BRIEF DESCRIPTION OF THE SEVERAL VIEWS OF THE DRAWINGS

The above and/or additional aspects and advantages of the present disclosure will be understood more apparently from the following description of embodiments with reference to the accompanied figures, in which.

DETAILED DESCRIPTION

Figure 1A:
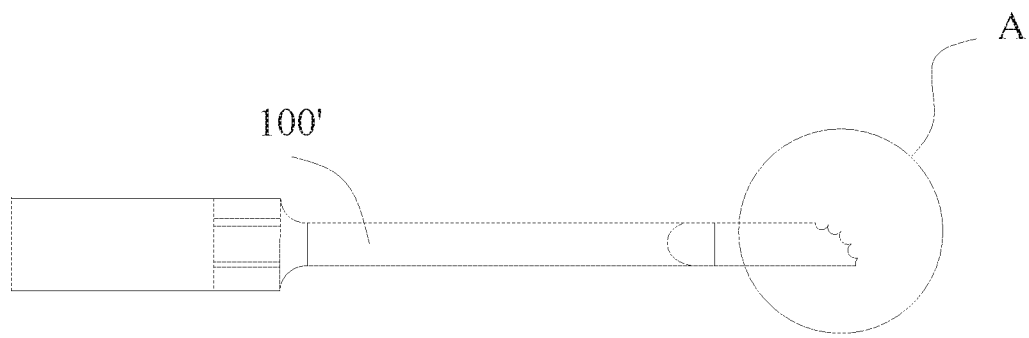
FIG. 1A is a schematic view showing a structure of a tool bit of an ultrasonic osteotome in the prior art.
Figure 1B:
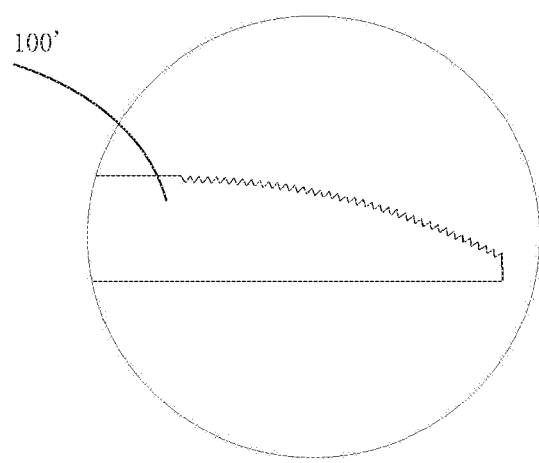
FIG. 1B is a local enlarged schematic view of part A shown in FIG. 1A.
Figure 2A:
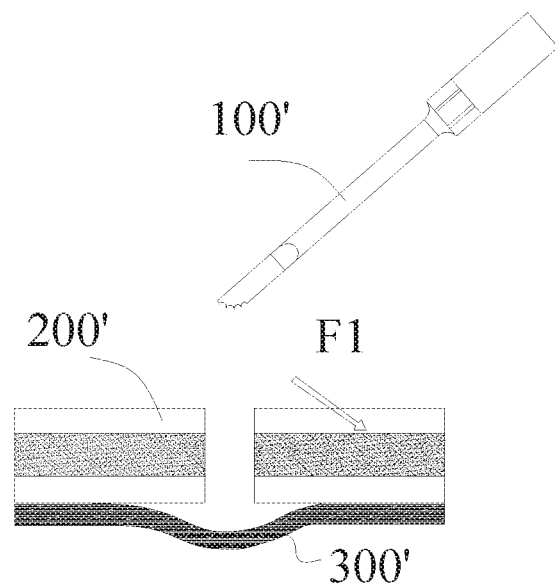
FIGS. 2A-2B are schematic views showing operations of the tool bit of the ultrasonic osteotome in the prior art.
Figure 2B:
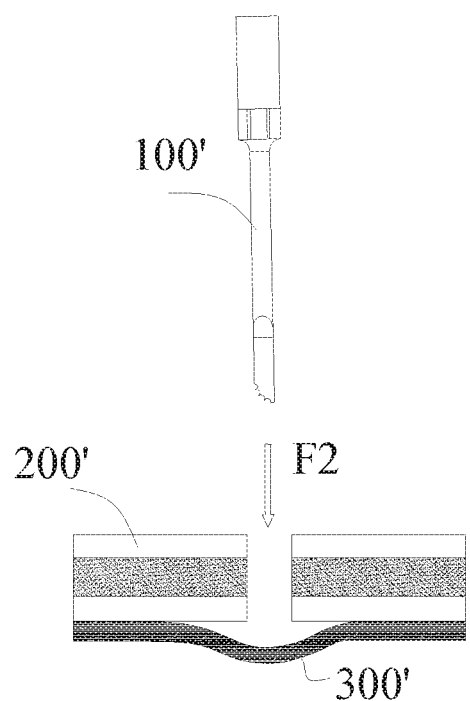

Next, the specific embodiments of the present invention will be described in detail with reference to accompanied figures. Throughout the description, identical or similar reference numerals represent identical or similar members. It should be noted that embodiments described herein are depicted only for illustration, instead of limiting to the present invention.

In the description of the present disclosure, it should be noted that the orientations or positions represented by the terms of "up", "down", "vertical", "horizontal", "top", "bottom", "inner" and "outer" and the like are based on the figures. It is given only by way of examples, instead of being intended to limit the device or element to have a special orientation or to be configured and operate in a special orientation. Thus, it cannot be understood as limiting of the present invention. In addition, the terms of "first" and "second" are depicted only by illustration, instead of being intended to define which one is more important or to define the number of the technical features. Thereby, the features defined by the terms of "first" and "second" may literally or impliedly include one or more features. In the description of the present disclosure, the term of "a plurality of" means two or more, unless it is explained otherwise.

In the description of the present disclosure, it should be noted that the terms of "mount", "connect" and "couple" should be understood in broad sense, unless they are defined or provided otherwise. For example, they may be used to describe a fixed connection, or a dismountable connection or an integral connection; they may be used to describe a mechanical connection, an electrical connection; they may be used to describe direct connection or connection by intermediate medium, or communication between interiors of two elements. The specific significations of the above terms in the present disclosure may be understood in the context by the skilled person in the art.

The technical solutions of the present disclosure will be further explained below with reference to figures and embodiments.

Figure 3:
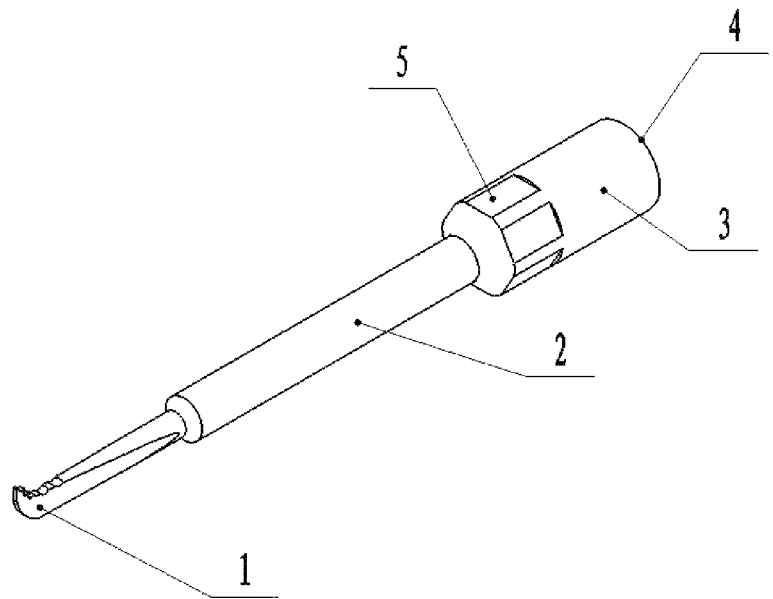
FIG. 3 is a schematic view showing a perspective structure of a tool bit of an ultrasonic osteotome in accordance with an embodiment of the present invention.
Figure 4:
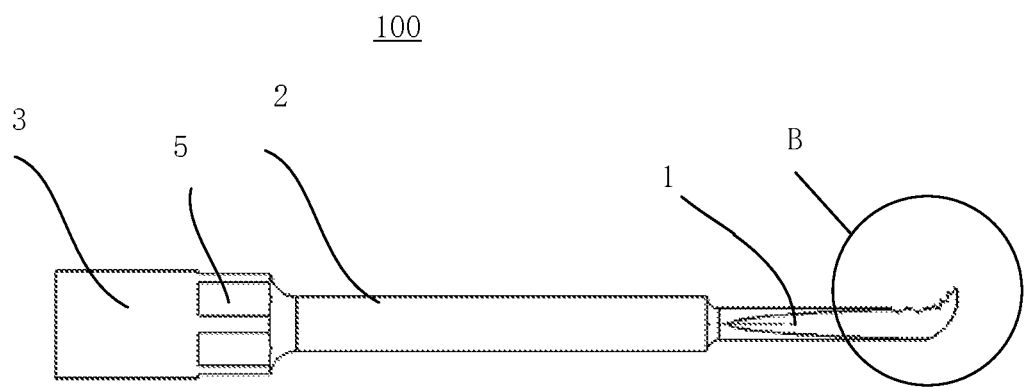
FIG. 4 is a front view of the tool bit of the ultrasonic osteotome in accordance with an embodiment of the present invention.
Figure 5:
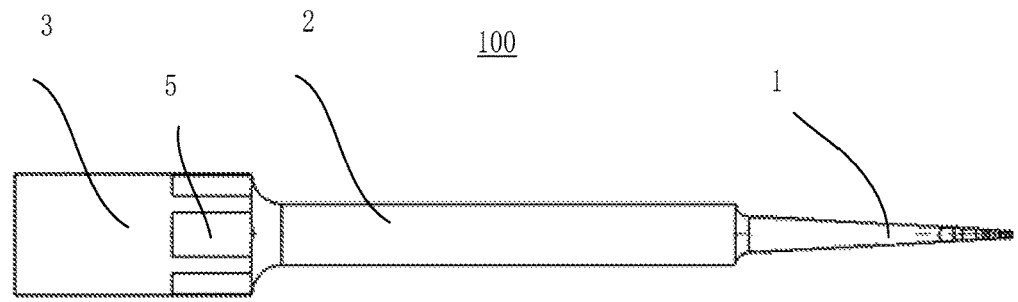
FIG. 5 is a top view of the tool bit of the ultrasonic osteotome in accordance with an embodiment of the present invention.

A tool bit of an ultrasonic osteotome in accordance with an embodiment of the present invention will below be described with reference to figures. FIG. 3 is a schematic view showing a perspective structure of a tool bit 100 of an ultrasonic osteotome in accordance with an embodiment of the present invention. FIG. 4 is a front view of the tool bit 100 of the ultrasonic osteotome in accordance with an embodiment of the present invention. FIG. 5 is a top view of the tool bit 100 of the ultrasonic osteotome in accordance with an embodiment of the present invention.

As a result of many years study, the inventors have found that an improvement in structure shape of the tool bit 100 of the ultrasonic osteotome can noticeably improve the usage security and efficiency. As illustrated in FIG. 3, in accordance with an embodiment of the present invention, the tool bit 100 of the ultrasonic osteotome may include an end portion 1 of the tool bit and an arbor 2. The end portion 1 of the tool bit is connected to a front end of the arbor 2. The end portion 1 of the tool bit has a hook-like shape, and includes a hook tip 11, a hook handle 13, as well as a hook-shaped interconnecting piece 12 which is interconnected between the hook tip 11 and the hook handle 13, as shown in FIGS. 3-6.

Figure 6:
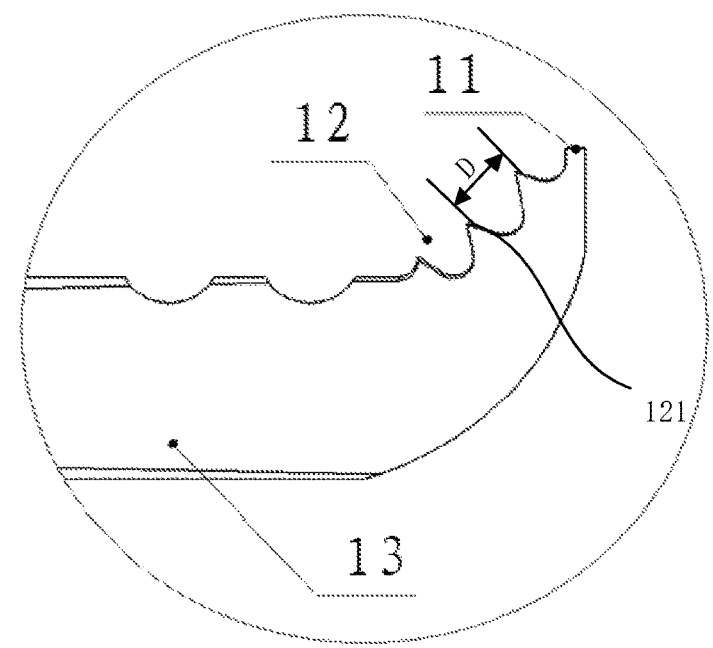
FIG. 6 is a schematic view showing a local enlarged structure of part B shown in FIG. 3.
Figure 7:
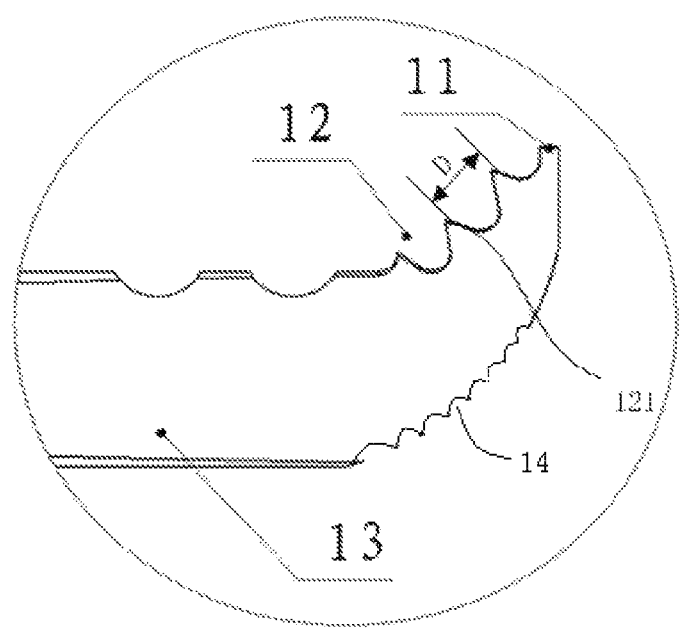
FIG. 7 is a schematic view showing a local enlarged structure of part B shown in FIG. 3, according to another embodiment.

In accordance with an embodiment of the present invention, the end portion 1 of the tool bit has a flat or tabular hook-like shape, as shown in FIG. 5. The end portion 1 of the tool bit includes the hook tip 11, the hook-shaped interconnecting piece 12 (or hook valley), and the hook handle 13, as shown in FIG. 6. The hook handle 13 is connected with the arbor 2, and the edge of the inner side of the hook-shaped interconnecting piece 12 is tooth-like. The cross section of hook handle 13 increases gradually in the direction from the hook-shaped interconnecting piece 12 to the arbor 2. Thus, the cantilever strength of the hook handle 13 is enhanced during operating process.

In accordance with some embodiments of the present invention, the outer side edge of the hook-shaped interconnecting piece 12 is tooth-like, that is, a plurality of grooves 14 are provided on the outer side edge of the hook-shaped interconnecting piece 12. Adjacent grooves define a tooth, and a plurality of grooves define a plurality of teeth, so as to make the outer side edge of the hook-shaped interconnecting piece 12 tooth-like. In this way, when the tool bit 100 of the ultrasonic osteotome is in use, not only the toothed inner side edge of the hook-shaped interconnecting piece 12 can be employed in abrasion cutting, but also the toothed outer side edge of the hook-shaped interconnecting piece 12 can be employed in it, so the usage convenience of the tool bit 100 of the ultrasonic osteotome can be improved.

In accordance with an embodiment of the present invention, the cross section of hook handle 13 is increased gradually in a direction extending towards hook-shaped interconnecting piece 12. Therefore, the hook tip 11 can be employed to accelerate the cutting speed in the process of cutting, and for the reason of being hook tip, accurately positioning can be realized during cutting operation with no skidding, so the chance of success in surgery can be improved.

In accordance with an embodiment of the present invention, the tool bit 100 of the ultrasonic osteotome further includes a bit body 3 which is connected to the arbor 2. The bit body 3 and the arbor 2 are connected via an arc transition. The bit body 3 is provided with a connecting thread 4 at an end portion thereof. In accordance with an embodiment of the present invention, for example, a hexagonal wrench-operation position 5 is provided on the bit body 3, so that a tool such as wrench etc. can be employed for fixing or fastening. When it needs to be used, the connecting thread 4 of this embodiment is connected to a special ultrasonic transducer (not shown) followed by the connection being tighten by a corresponding wrench. And then the ultrasonic transducer is connected to a special ultrasonic machine and thereby an ultrasonic operating may be available. In accordance with an embodiment of the present invention, as shown in FIG. 4, the arbor 2 and the end portion 1 can be formed as an integral part, so as to decrease manufacture cost. Furthermore, the end portion 1, the arbor 2, and saidbit body 3 can be integrally formed.

As shown in FIG. 6, among the teeth provided on the inner side of the hook-shaped interconnecting piece 12, tooth pitch D of adjacent said teeth increases gradually from the hook tip to the hook handle.

The operation of the tool bit of the ultrasonic osteotome according to an embodiment of the present invention will be described below with reference to FIGS. 8-9. When bones need to be cut and said hooked tool bit 100 of the ultrasonic osteotome is operated, said hooked tool bit 100 can be used the same as using a hook to hook something, or can be used as a sickle, and also can be used by means of other arbitrary mode. The hook tip 11 of the end portion 1 of the hooked tool bit can be used to cut directly. When the hook tip 11 is used to cut, the hook handle 13 acts to fix a position, so as to ensure the cutting depth of the tool bit, and to protect the surrounding bone tissue. In this way, said tool bit 100 of the ultrasonic osteotome can be easily positioned, and can be operated conveniently. Because said end portion 1 of the tool bit is structured to be a tabular hook-shape, it is convenient for a user to position during operation.

In accordance with an embodiment of the present invention, when being in use, the hook tip 11 can also be used to fix a position, and can be used to abut against an upper edge or a lower edge of a bone, then the tooth-like inner side edge of hook-shaped interconnecting 12 cuts the bone, the hook handle and hook tip act to fix a position simultaneously. The direction, in which a force being exerted, is parallel to the bone surface, or extends towards upper and behind. In this way, in the process of cutting, a fulcrum can be formed on basis of the hook tip 11, and a cutting can be implemented along this fulcrum. Such design has an advantage that the surrounding bore tissue can be protected, and the cutting depth and cutting thickness can be controlled accurately.

Figure 8:
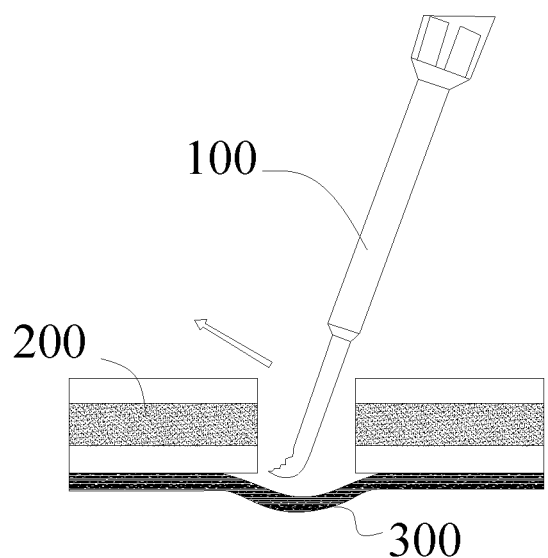
FIG. 8 is a schematic view showing the tool bit of the ultrasonic osteotome in a usage state in accordance with an embodiment of the present invention.
Figure 9:
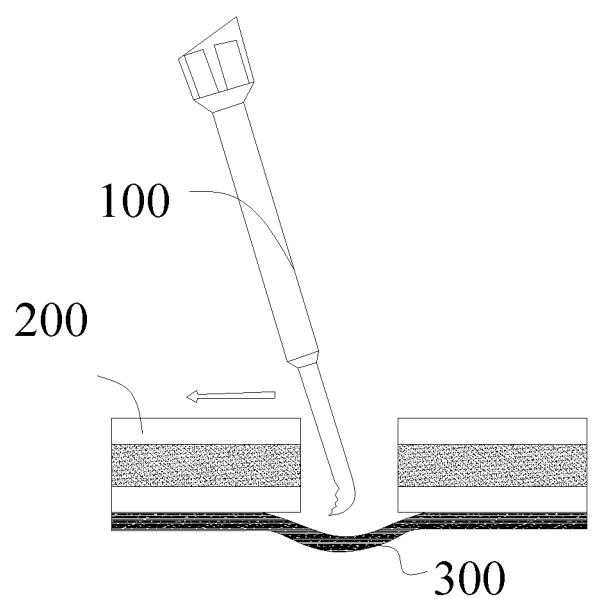
FIG. 9 is a schematic view showing the tool bit of the ultrasonic osteotome in another usage state in accordance with an embodiment of the present invention.

If the tool bit 100 of the ultrasonic osteotome is used in surgery, the hook tip 11 can be extended into between spinal dural and vertebrate body (bone) to be removed, as shown in FIG. 8. Then the hook tip 11 abuts against the bone 200 and forms a fulcrum, and the hook tip 11 is operated by exerting forces from inner side to outer side. Therefore, the risk of accidentally destroying or injuring a soft issue 300 (such as spinal dural etc.) is reduced, then unrecoverable permanent damage to marrow is avoided. Therefore, the risk of surgery is decreased, and the difficulty of operation drops. This is especially suitable for removing an entire bone which can be restored later. As shown in FIG. 9, the hooked-shape tool bit 100 of the ultrasonic osteotome is used to propel the bone 200 from right to left, at this time, the hook tip 11 serves as a fulcrum and forces are exerted from left to right, therefore, even if deviation happens, the tool bit 100 of the ultrasonic osteotome will move towards outside, with the hurt to the soft tissue 300 being avoided.

Moreover, the present invention further provides an ultrasonic osteotome comprising the tool bit as described in any of the above embodiments. Said ultrasonic osteotome can be employed to cut bones by use of its hook-tip, with high efficiency and short surgery time. The labour intensity of medical workers is decreased, and accurate positioning can be realized in cutting process, with no skidding. The ultrasonic osteotome according to the embodiment of the present invention is exquisitely and compactly designed, and the cutting amount and cutting shape for the bone can be controlled accurately, so the bone wastage resulting from cutting in surgery is decreased. Furthermore, the ultrasonic osteotome according to the embodiment of the present invention has a hemostasis effect, so the amount of bleeding is decreased. Moreover, the tool bit of the ultrasonic osteotome according to the embodiment of the present invention can be machined easily with low manufacture cost.

In the above description, the terms of "an embodiment", "some embodiments", "exemplary embodiment", "example", "specific example" or "some examples" mean that the specific features, structures, materials or characteristics described in the embodiment or example may be contained in at least one embodiment or example of the present invention. In the description, the exemplary expression for the above terms is not necessarily limited to the same embodiment or example. And the specific features, structures, materials or characteristics described may be combined in any suitable means in any of one or more embodiments or examples.

Although some embodiments of the general inventive concept are illustrated and explained, it would be appreciated by those skilled in the art that modifications, replacements, alternations and variations may be made in these embodiments without departing from the principles and spirit of the general inventive concept of the disclosure, the scope of which is defined in the appended claims and their equivalents.

What is claimed is:

1. A tool bit of an ultrasonic osteotome, comprising:
an arbor; and
an end portion of the tool bit connected to a front end of said arbor,
said end portion of the tool bit has a sickle-like shape and includes a hook tip, a hook handle, as well as a hook-shaped interconnecting piece which is curved and interconnected between said hook tip and said hook handle,
wherein said hook handle is connected with said arbor, and an inner side edge of said hook-shaped interconnecting piece is tooth-like; and
wherein among teeth provided on the inner side edge of said hook-shaped interconnecting piece, a tooth pitch of adjacent said teeth increases gradually from said hook tip to said hook handle.

2. The tool bit according to claim 1, wherein an outer side edge of said hook-shaped interconnecting piece is tooth-like.

3. The tool bit according to claim 1, wherein the end portion of the tool bit is structured to have a tabular hook-like shape.

4. The tool bit according to claim 3, wherein a cross section of said hook handle increases gradually in a direction from said hook-shaped interconnecting piece to said arbor.

5. The tool bit according to claim 4, wherein a cross section of said hook tip increases gradually in a direction extending towards said hook-shaped interconnecting piece.

6. The tool bit according to claim 1, further comprising:
a bit body connected to said arbor,
wherein said bit body and said arbor are connected via an arc transition, and said bit body is provided with a wrench-operation position.

7. The tool bit according to claim 6, wherein said end portion of the tool bit, said arbor and said bit body are formed as an integral part.

8. The tool bit according to claim 1, wherein said arbor and said end portion of the tool bit are formed as an integral part.

9. An ultrasonic osteotome comprising a tool bit, the tool bit comprising;
an arbor; and
an end portion of the tool bit connected to a front end of said arbor,
said end portion of the tool bit has a sickle-like shape and includes a hook tip, a hook handle, as well as a hook-shaped interconnecting piece which is curved and interconnected between said hook tip and said hook handle,
wherein said hook handle is connected with said arbor, and an inner side edge of said hook-shaped interconnecting piece is tooth-like;
wherein among teeth provided on the inner side edge of said hook-shaped interconnecting piece, a tooth pitch of adjacent said teeth increases gradually from said hook tip to said hook handle.

* * * * *